United States Patent
Weiner et al.

(10) Patent No.: US 7,625,751 B2
(45) Date of Patent: Dec. 1, 2009

(54) WNV CORE PROTEIN/CAPSID INTERACTING PROTEIN AND USES OF THE SAME

(75) Inventors: David B. Weiner, Merion Station, PA (US); Mathura P. Ramanathan, Ardmore, PA (US); Joo-Sung Yang, Seoul (KR)

(73) Assignee: The Trustees of The University of Pennsylvania, Philadelphia, PA (US)

( * ) Notice: Subject to any disclaimer, the term of this patent is extended or adjusted under 35 U.S.C. 154(b) by 508 days.

(21) Appl. No.: 10/478,743

(22) PCT Filed: May 28, 2002

(86) PCT No.: PCT/US02/16692

§ 371 (c)(1),
(2), (4) Date: Sep. 9, 2004

(87) PCT Pub. No.: WO02/097043

PCT Pub. Date: Dec. 5, 2002

(65) Prior Publication Data

US 2006/0088824 A1    Apr. 27, 2006

Related U.S. Application Data

(60) Provisional application No. 60/293,569, filed on May 25, 2001.

(51) Int. Cl.
*C12N 15/12* (2006.01)
*C12N 5/10* (2006.01)
*C12N 1/21* (2006.01)
*C07H 21/00* (2006.01)

(52) U.S. Cl. ................ 435/320.1; 435/325; 435/252.3; 536/23.5; 536/24.31

(58) Field of Classification Search ..................... 435/6, 435/5; 514/364
See application file for complete search history.

(56) References Cited

U.S. PATENT DOCUMENTS 6,031,151 A * 2/2000 Draper ....................... 800/298

FOREIGN PATENT DOCUMENTS

EP    1033401 A2 *  9/2000

OTHER PUBLICATIONS

Fiscella et al., "Wip1, a novel human protein phosphatase that is induced in response to ionizing radiation in a p53-dependent manner," PNAS, vol. 94, pp. 6048-6053 (1997).*
Bressan et al., "Repeating Structure of Chick Tropoelastin Revealed by Complementary DNA Cloning," Biochemistry, vol. 26, No. 6 (1987).*
NCBI Blast nucleotide search result, Accession No. AE014298 (search was run 2007).*
NCBI Blast nucleotide search result, Accession No. M15889.1 (search was run 2007).*
SCORE sequence search result 14, 3.rng (2007).*
Genome Research 8:1097-1108, 1998 (no author listed).*
Accession No. NM_031288, Sep. 24, 2005.*
Genbank AW594669, Mar. 22, 2000.*
EMBL Acc. No. AB054538 from Ariga, et al., "*Homo spaiens* mRNA for PAPA-1, complete cds," Jan. 21, 2001.
EMBL Acc. No, AW594669 from National Cancer Institute Genome Anatomy Project, "*Homo sapiens* cDNA clone," Mar. 3, 2000.
Ramanathan, et al., "Identification of a novel cellular receptor protein, Wip as a ligand for the West Nile Virus capsid," Abstracts of the General Meeting of the American Society for Microbiology, (2002) 102:474.
Takekawa, et al., "p-53 inducible Wip1 phosphatase mediates a negative feedback regulation of p38 MAPK-p53 signalling in response to UV radiation," EMBO J. (2000) 19:6517-6526.
Choi, et al., "The structure and expression of the murine wildtype p53-induced phosphatase 1 (Wip1) gene," Genomics (2000) 64:298-306.
Sambrook, et al., *Molecular Cloning: A Laboratory Manual*, Second Ed. (New York: Col Spring Harbor Press, 1989).
Innis, M.A., et al., Eds., *PCR Protocols: A Guide to Methods and Applications* (San Diego, CA: Academic Press, Inc., 1990).
Erlich, H.A., et al., Eds., "Polymerase Chain Reaction" (Cold Spring Harbor, NY: Cold Spring Harbor Press, 1989).
Accession No. NM 018739 (PAP-1; Mouse), Nov. 17, 2006.
Accession No. D78255 (PAP-1; Mouse), Feb. 1, 2003.
Accession No. M24779 (PIM-1; Human), Nov. 16, 1995.
Accession No. NM 002648 (PIM-1; Human), Nov. 17, 2006.
Accession No. XM 004317 (PIM-1; Human), Apr. 16, 2001.
Accession No. AB054538 (PAPA-1 (WIP-1)); Human), Nov. 18, 2006.
Accession No. NM 031288 (Papa-1 (WIP-1)); Human), Nov. 18, 2006.
Accession No. AF202541 (strain HNY1999), Dec. 16, 1999.
Accession No. NC 001563 (complete genome), Nov. 2, 2006.
Harlow, E. and Lane, D., *Antibodies: A Laboratory Manual* (Cold Spring Harbor, NY: Cold Spring Harbor Laboratory, 1988).

* cited by examiner

*Primary Examiner*—Mary E Mosher
(74) *Attorney, Agent, or Firm*—Pepper Hamilton LLP

(57) ABSTRACT

Substantially pure WIP-1 and its use in assays to identify PAP-1/WIP-1 interaction inhibitors or WIP-I/WNV Cp interaction inhibitors are disclosed. Compositions comprising antisense sequences to prevent expression of WIP-1 and methods of treating cancer using the same are disclosed.

11 Claims, 3 Drawing Sheets

FIGURE 1

Identification of an intracellular receptor for the West Nile Virus Capsid protein(WNVCp)

Through Yeast-two hybrid system a cDNA encoding a novel protein called Wip-1 has been cloned.

WNVCp interacts with Wip-1 protein.

Wip-1 gene is 1032bp in length that encodes 343 aa-length protein of 37.8kDa molecular mass.

Wip-1 is a first protein to be identified and molecularly characterized to be the human cellular legand for the WNVCp protein.

Wip-1 protein has been identified very recently in Jan 2001 as an interacting protein partner for Pap 1 which is the legand for the protein product of the proto-oncogene, *pim-1*.

HA-PAPA1 -> 1-phase Translation

DNA sequence    1160 b.p.    ACCATGCCATAC ... aaaaaaaaaaaa    linear

```
1/1                                      31/11
ACC ATG CCA TAC GAC GTA CCA GAT TAC GCT  CAT ATG GAG GCC CCT GAG CCG GGA GAA GCC
 T   M   P   Y   D   V   P   D   Y   A    H   M   E   A   P   E   P   G   E   A
61/21                                    91/31
CTG GAG TTG AGC Ctg gcg ggt gcc cat ggc  cat gga gtg cac aag aaa aaa cac aag aag
 L   E   L   S   L   A   G   A   H   G    H   G   V   H   K   K   K   H   K   K
121/41                                   151/51
cac aag aag aaa cac aag aag aaa cac cat  cag gaa gaa gac gcc ggg ccc acg cag ccg
 H   K   K   K   H   K   K   K   H   H    Q   E   E   D   A   G   P   T   Q   P
181/61                                   211/71
tcc cct gcc aag cct cag ctc aaa ctc aaa  atc aag ctt ggg gga caa gtc ctg ggg acc
 S   P   A   K   P   Q   L   K   L   K    I   K   L   G   G   Q   V   L   G   T
241/81                                   271/91
aag agt gtt cct acc ttc act gtg atc cca  gag ggg cct cgc tca ccc tct ccc ctt atg
 K   S   V   P   T   F   T   V   I   P    E   G   P   R   S   P   S   P   L   M
301/101                                  331/111
gtt gtg gat aat gaa gag gaa cct atg gaa  gga gtc ccc ctt gag cag tac cgt gcc tgg
 V   V   D   N   E   E   E   P   M   E    G   V   P   L   E   Q   Y   R   A   W
361/121                                  391/131
ctg gat gaa gac agt aat ctc tct ccc tct  cca ctt cgg gac cta tca gga ggg tta ggg
 L   D   E   D   S   N   L   S   P   S    P   L   R   D   L   S   G   G   L   G
421/141                                  451/151
ggt cag gag gaa gag gag gaa cag agg tgg  ctc gat gcc ctg gag aag ggg gag ctg gat
 G   Q   E   E   E   E   Q   R   W    L   D   A   L   E   K   G   E   L   D
481/161                                  511/171
gac aat gga gac ctc aag aag gag atc aat  gag cgg ctg ctt act gct cga cag cga gct
 D   N   G   D   L   K   K   E   I   N    E   R   L   L   T   A   R   Q   R   A
541/181                                  571/191
ctg ctc cag aag gcg cgg agt caa cct tcc  cct atg ctg ccg ctg cct gta gct gag ggc
 L   L   Q   K   A   R   S   Q   P   S    P   M   L   P   L   P   V   A   E   G
601/201                                  631/211
tgc cca cct ccc gcc ctc aca gag gag atg  ctg ctg aag cgc gag gag cgg gcg cgg aag
 C   P   P   P   A   L   T   E   E   M    L   L   K   R   E   E   R   A   R   K
661/221                                  691/231
cgg cgg ctc cag gcg gcg cgg cgg gca gaa  gag cac aag aac cag act atc gag cgc ctc
 R   R   L   Q   A   A   R   R   A   E    E   H   K   N   Q   T   I   E   R   L
721/241                                  751/251
acc aag act gcg gcg acc agt ggg cgg gga  ggc cgg ggg ggc gca cgg ggc gag cgg cgg
 K   T   A   A   T   S   G   R   G    G   R   G   G   A   R   G   E   R   R
81/261                                   811/271
ga ggg cgg gct gcg gct ccg gcc ccc atg  gtg cgc tac tgc agc gga gca cag ggt tcc
 G   R   A   A   A   P   A   P   M    V   R   Y   C   S   G   A   Q   G   S
41/281                                   871/291
cc ctt tcc ttc cca cct ggc gtc ccc gcc  ccc acg gca gtg tct cag cgg cca tcc ccc
 L   S   F   P   P   G   V   P   A    P   T   A   V   S   Q   R   P   S   P
901/301                                  931/311
tca ggc ccg ccg ctg cgc tgc tct gtc ccc  ggc tgt ccc cat ccg cgc cgc tac gct tgc
 S   G   P   P   P   R   C   S   V   P    G   C   P   H   P   R   R   Y   A   C
961/321                                  991/331
tcc cgc aca ggc cag gca ctc tgt agt ctt  cag tgc tac cgc atc aac ctg cag atg cgg
 S   R   T   G   Q   A   L   C   S   L    Q   C   Y   R   I   N   L   Q   M   R
1021/341                                 1051/351
ctg ggg ggg ccc gag ggt cct gga tcc ccc  ctt ttg gct acg taa ggc cct taa ccc gga
 L   G   G   P   E   G   P   G   S   P    L   L   A   T   *   G   P   *   P   G
1081/361                                 1111/371
ctc tgc gcc ccg tcc cat gcc cgc tct tga  gta tct tcc cca ccc tat taa att aca tcc
 L   C   A   P   S   H   A   R   S   *    V   S   S   P   P   Y   *   I   T   S
1141/381
ggt gca aaa aaa aaa aaa aa
 G   A   K   K   K   K
```

AB054538.
    source    1..1164
    gene      38..1069
    CDS       38..1069

MEAPEPGEALELSLAGAHGHGVHKKKHKKHKKKHKKKHHQEEDA
GPTQPSPAKPQLKLKIKLGGQVLGTKSVPTFTVIPEGPRSPSPLMVVDNEEEPMEGVP
LEQYRAWLDEDSNLSPSPLRDLSGGLGGQEEEEEQRWLDALEKGELDDNGDLKKEINE
RLLTARQRALLQKARSQPSPMLPLPVAEGCPPPALTEEMLLKREERARKRRLQAARRA
EEHKNQTIERLTKTAATSGRGGRGGARGERRGGRAAAPAPMVRYCSGAQGSTLSFPPG
VPAPTAVSQRPSPSGPPPRCSVPGCPHPRRYACSRTGQALCSLQCYRINLQMRLGGPE
GPGSPLLAT

```
   1 gggtaagctg tggcggcgtg ggagcacctc tggggctatg gaggcccctg agccgggaga
  61 agccctggag ttgagcctgg cgggtgccca tggccatgga gtgcacaaga aaaaacacaa
 121 gaagcacaag aagaaacaca agaagaaaca ccatcaggaa gaagacgccg ggcccacgca
 181 gccgtcccct gccaagcctc agctcaaact caaaatcaag cttggggggac aagtcctggg
 241 gaccaagagt gttcctacct tcactgtgat cccagagggg cctcgctcac cctctcccct
 301 tatggttgtg gataatgaag aggaacctat ggaaggagtc ccccttgagc agtaccgtgc
 361 ctggctggat gaagacagta atctctctcc ctctccactt cgggacctat caggagggtt
 421 aggggggtcag gaggaagagg aggaacagag gtggctggat gccctggaga aggggggagct
 481 ggatgacaat ggagacctca agaaggagat caatgagcgg ctgcttactg ctcgacagcg
 541 agctctgctc cagaaggcgc ggagtcaacc ttcccctatg ctgccgctgc ctgtagctga
 601 gggctgccca cctcccgccc tcacagagga gatgctgctg aagcgcgagg agcgggcgcg
 661 gaagcggcgg ctccaggcgg cgcggcgggc agaagagcac aagaaccaga ctatcgagcg
 721 cctcaccaag actgcggcga ccagtgggcg gggaggccgg ggggcgcac ggggcgagcg
 781 gcggggaggg cgggctgcgg ctccggcccc catggtgcgc tactgcagcg gagcacaggg
 841 ttccacccct tccttcccac ctggcgtccc cgcccccacg gcagtgtctc agcggccatc
 901 cccctcaggc ccgccgccgc gctgtctctgt ccccggctgt ccccatccgc gccgctacgc
 961 ttgctcccgc acaggccagg cactctgtag tcttcagtgc taccgcatca acctgcagat
1021 gcggctgggg gggcccgagg gtcctggatc ccccctttg gctacgtaag gcccttaacc
1081 cggactctgc gccccgtccc atgcccgctc ttgagtatct tccccaccct attaaattac
1141 atccggtgca aaaaaaaaaa aaaa
```

WNV CORE PROTEIN/CAPSID INTERACTING PROTEIN AND USES OF THE SAME

CROSS REFERENCE TO RELATED APPLICATION

This application is a U.S. National Phase Application of PCT International Application PCT/US02/16692 filed May 28, 2002 which claims priority to U.S. Provisional Application No. 60/293,569, filed May 25, 2001.

FIELD OF THE INVENTION

The invention relates to the identification and cloning of human protein which binds to WNV capsid, to methods of making and using the same, and to compositions and methods of inhibiting their activity in the cell cycle.

BACKGROUND OF THE INVENTION

The core protein of West Nile virus (WNV), also referred to as the capsid or Cp, has recently been identified as being capable of inducing apoptosis in cell in which it is present. This observation is described in PCT/US01/31355 and Ser. No. 60/237,885, which are each incorporated herein by reference.

There is a need to identify novel compounds which inhibit WNV replication. Specifically, safe and effective compounds are sought which reduce replication by interfering with particular molecular signals mediated by WNV capsid protein. Likewise, safe and effective compounds are sought which interfere with the cofactor with which WNV Cp interacts, which is an essential component of the cell cycle cascade. Moreover, there is a need to identify the co-factor and target it in methods of modulating the cell cycle. There is a need for compounds and methods for inhibiting the activity of WNV Cp.

SUMMARY OF THE INVENTION

The present invention relates to substantially pure WIP-1, to recombinant expression vectors comprising a nucleic acid sequence that encodes and host cells that comprise the recombinant expression vector.

The present invention relates to isolated nucleic acid molecules consisting of the WIP-1 cDNA sequence or a fragment thereof having at least 10 nucleotides, or a nucleotide sequence complementary to a nucleotide sequence of at least 10 nucleotides of the WIP-1 cDNA sequence.

The present invention relates to isolated antibodies which binds to an epitope on the WIP-1.

The present invention relates to methods of identifying compounds that inhibit WNV Cp binding to WIP-1.

The present invention relates to methods of identifying compounds that inhibit PAP-1 binding to WIP-1.

The present invention relates to methods of treating an individual who has tumor cells with PAP-1 associated with WIP-1 comprising administering to said individual a composition which comprises a compound that prevents WIP-1 expression or WIP-1/PAP-1 interaction.

BRIEF DESCRIPTION OF FIGURES

FIG. 1 shows the various interactions of WIP-1, PAP-1, WNV Cp and PIM-1.

FIG. 2 shows the cDNA and amino acid sequences of WIP-1 including the HA fusion sequences (SEQ ID NO:1 and SEQ ID NO:2).

FIG. 3 shows the cDNA and amino acid sequences of WIP-1 (SEQ ID NO:1 and SEQ ID NO:2).

DETAILED DESCRIPTION OF PREFERRED EMBODIMENTS

It has been discovered that WNV Cp binds to a protein called WNV Capsid Protein/Core Interacting Protein 1 (WIP-1) which associates with an oncogene referred to as PAP-1. It has been discovered that WNV Cp induces apoptosis. Accordingly, the modulation of interaction between WNV Cp and WIP-1 may inhibit WNV activity. Moreover, binding to WIP-1 or otherwise inhibiting its association with PAP1 may induce apoptosis.

As used herein, WIP-1 is used interchangeably throughout with PAPA-1 and each designation refers to the same gene and protein as the other. This application claims priority to U.S. Provisional Application No. 60/293,569 which is incorporated herein by reference.

The discovery that WIP-1 binds to the apoptosis inducing protein WNV Cp the means to design and discover specific inhibitors. According to the present invention, WIP-1 may be used to screen compounds for specific inhibitors. Inhibitors are useful as anti-WNV agents. Purified WIP-1, and complexes which include WIP-1, may be used in drug screens to determine whether or not these proteins and complexes are active in the presence of test compounds. Test compounds may be screened to identify compounds which dissociate the complexes and inhibit the formation of complexes.

WIP-1 is an interacting protein of PAP-1, a ligand for the proto-oncogene PIM-1. FIG. 1 shows the various interactions. The discovery that when WIP-1 binds to the apoptosis inducing protein WNV Cp provides a means to design and discover specific inhibitors of WIP-1/PAP-1 interactions as well as a target for inducing apoptosis in tumor cells which have WIP-1/PAP-1 complexes. According to the present invention, WIP-1 may be used to screen compounds for specific inhibitors of WIP-1/PAP-1 interactions. Inhibitors are useful as anti-cancer agents. Purified WIP-1, and complexes which include WIP-1, may be used in drug screens to determine whether or not these proteins and complexes are active in the presence of test compounds. Test compounds may be screened to identify compounds which dissociate the complexes and inhibit the formation of complexes.

Isolated cDNA that encodes WIP-1 is useful as a starting material in the recombinant production of WIP-1. The cDNA is incorporated into vectors including expression vectors which are introduced into host cells that then express the proteins recombinantly. Nucleic acid molecules and fragments thereof, particularly genomic sequences may be used as probes to detect genetic rearrangements. Probes are useful, for example, in restriction fragment length polymorphism assays and fluorescence in situ hybridization assays. Nucleic acid molecules which comprise a nucleotide sequence which are complementary to fragments of the cDNA that encode WIP-1 may be used as antisense molecules and primers to inhibit translation of mRNA and amplify genetic sequences, respectively.

WIP-1 is encoded by cDNA shown in FIG. 2 which also lists the amino acid sequence of WIP-1 can be isolated from natural sources, produced by recombinant DNA methods or synthesized by standard protein synthesis techniques.

Using standard techniques and readily available starting materials, a nucleic acid molecule that encodes WIP-1 may be isolated from a cDNA library, using probes and primers which are designed using the nucleotide sequence information disclosed. The present invention relates to an isolated nucleic acid molecule that comprises a nucleotide sequence that encodes WIP-1. The present invention relates to an isolated nucleic acid molecule that comprises a nucleotide sequence that encodes the amino acid sequence of WIP-1, or a fragment thereof. In some embodiments, the nucleic acid molecules consist of a nucleotide sequence that encodes WIP-1. In some embodiments, the nucleic acid molecules comprise the nucleotide sequence that consists of the coding sequence of WIP-1 or complimentary sequences thereof. In some embodiments, the nucleic acid molecules consist of the nucleotide sequence set that encodes WIP-1. The isolated nucleic acid molecules of the invention are useful to prepare constructs and recombinant expression systems for preparing proteins of the invention.

A cDNA library may be generated by well known techniques. A cDNA clone which contains one of the nucleotide sequences described herein may be identified using probes or primers that comprise at least a portion of the nucleotide sequence that encodes WIP-1. The probes or primers have at least 16 nucleotides, preferably at least 24 nucleotides. The probes or primers are used to screen the cDNA library using standard hybridization techniques. Alternatively, genomic clones may be isolated using genomic DNA from any human cell as a starting material.

The present invention relates to isolated nucleic acid molecules that comprise a nucleotide sequence identical or complementary to a fragment of WIP-1 which is at least 10 nucleotides. In some embodiments, the isolated nucleic acid molecules consist of a nucleotide sequence identical or complementary to a fragment of WIP-1 which is at least 10 nucleotides. In some embodiments, the isolated nucleic acid molecules comprise or consist of a nucleotide sequence identical or complementary to a fragment of WIP-1 which is 15-150 nucleotides. In some embodiments, the isolated nucleic acid molecules comprise or consist of a nucleotide sequence identical or complementary to a fragment of SEQ ID NO:1 or which is 15-30 nucleotides. Isolated nucleic acid molecules that comprise or consist of a nucleotide sequence identical or complementary to a fragment of WIP-1 which is at least 10 nucleotides are useful as probes for identifying genes and cDNA sequence of WIP-1. PCR primers for amplifying WIP-1 genes and WIP-1 cDNA, and antisense molecules for inhibiting transcription and translation of WIP-1 genes and WIP-1 cDNA, respectively, which encode WIP-1. The antisense molecules for inhibiting transcription and translation of WIP-1 may be incorporated into a pharmaceutical composition useful to treat cancer.

The cDNA that encodes WIP-1 may be used as a molecular marker in electrophoresis assays in which cDNA from a sample is separated on an electrophoresis gel and WIP-1 probes are used to identify bands which hybridize to such probes. The isolated nucleic acid molecule provided as a size marker will show up as a positive band which is known to hybridize to the probes and thus can be used as a reference point to the size of cDNA that encodes WIP-1. Electrophoresis gels useful in such an assay include standard polyacrylamide gels as described in Sambrook et al., *Molecular Cloning a Laboratory Manual*, Second Ed. Cold Spring Harbor Press (1989) which is incorporated herein by reference.

The nucleotide sequences of WIP-1 may be used to design probes, primers and complementary molecules which specifically hybridize to the unique nucleotide sequences of WIP-1. Probes, primers and complementary molecules which specifically hybridize to nucleotide sequence that encodes WIP-1 may be designed routinely by those having ordinary skill in the art.

The present invention also includes labeled oligonucleotides which are useful as probes for performing oligonucleotide hybridization methods to identify WIP-1. Accordingly, the present invention includes probes that can be labeled and hybridized to unique nucleotide sequences of WIP-1. The labeled probes of the present invention are labeled with radiolabeled nucleotides or are otherwise detectable by readily available nonradioactive detection systems. In some preferred embodiments, probes comprise oligonucleotides consisting of between 10 and 100 nucleotides. In some preferred, probes comprise oligonucleotides consisting of between 10 and 50 nucleotides. In some preferred, probes comprise oligonucleotides consisting of between 12 and 20 nucleotides. The probes preferably contain nucleotide sequence completely identical or complementary to a fragment of a unique nucleotide sequences of WIP-1. In some embodiments, labeled probes are used to determine on which chromosome the WIP-1 gene is present.

The cDNA that encodes WIP-1 may be used to design PCR primers for amplifying nucleic acid sequences. PCR technology is practiced routinely by those having ordinary skill in the art and its uses in diagnostics are well known and accepted. Methods for practicing PCR technology are disclosed in "PCR Protocols: A Guide to Methods and Applications", Innis, M. A., et al. Eds. Academic Press, Inc. San Diego, Calif. (1990) which is incorporated herein by reference. Applications of PCR technology are disclosed in "Polymerase Chain Reaction" Erlich, H. A., et al., Eds. Cold Spring Harbor Press, Cold Spring Harbor, N.Y. (1989) which is incorporated herein by reference. Some simple rules aid in the design of efficient primers. Typical primers are 18-28 nucleotides in length having 50% to 60% g+c composition. The entire primer is preferably complementary to the sequence it must hybridize to. Preferably, primers generate PCR products 100 base pairs to 2000 base pairs. However, it is possible to generate products of 50 base pairs to up to 10 kb and more.

PCR technology allows for the rapid generation of multiple copies of nucleotide sequences by providing 5' and 3' primers that hybridize to sequences present in a nucleic acid molecule, and further providing free nucleotides and an enzyme which fills in the complementary bases to the nucleotide sequence between the primers with the free nucleotides to produce a complementary strand of DNA. The enzyme will fill in the complementary sequences adjacent to the primers. If both the 5' primer and 3' primer hybridize to nucleotide sequences on the complementary strands of the same fragment of nucleic acid, exponential amplification of a specific double-stranded product results. If only a single primer hybridizes to the nucleic acid molecule, linear amplification produces single-stranded products of variable length.

The present invention relates to a vector or a recombinant expression vector that comprises a nucleotide sequence that encodes WIP-1. As used herein, the term "recombinant expression vector" is meant to refer to a plasmid, phage, viral particle or other vector which, when introduced into an appropriate host, contains the necessary genetic elements to direct expression of the coding sequence that encodes WIP-1.

One having ordinary skill in the art can isolate the nucleic acid molecule that encodes WIP-1 and insert it into an expression vector using standard techniques and readily available starting materials. The coding sequence is operably linked to the necessary regulatory sequences. Expression vectors are well known and readily available. Examples of expression vectors include plasmids, phages, viral vectors and other nucleic acid molecules or nucleic acid molecule containing vehicles useful to transform host cells and facilitate expression of coding sequences. The recombinant expression vectors of the invention are useful for transforming hosts which express WIP-1.

The present invention relates to a host cell that comprises the recombinant expression vector that includes a nucleotide sequence that WIP-1. Host cells for use in well known recombinant expression systems for production of proteins are well known and readily available. Examples of host cells include bacteria cells such as E. coli, yeast cells such as S. cerevisiae, insect cells such as S. frugiperda, non-human mammalian tissue culture cells chinese hamster ovary (CHO) cells and human tissue culture cells such as HeLa cells.

In some embodiments, for example, one having ordinary skill in the art can, using well known techniques, insert DNA molecules into a commercially available expression vector for use in well known expression systems. For example, the commercially available plasmid pSE420 (Invitrogen, San Diego, Calif.) may be used for production of WIP-1 in E. coli. The commercially available plasmid pYES2 (Invitrogen, San Diego, Calif.) may, for example, be used for production in S. cerevisiae strains of yeast. The commercially available MAXBAC™ complete baculovirus expression system (Invitrogen, San Diego, Calif.) may, for example, be used for production in insect cells. The commercially available plasmid pcDNA I or pcDNA3 (Invitrogen, San Diego, Calif.) may, for example, be used for production in mammalian cells such as Chinese Hamster Ovary cells. One having ordinary skill in the art can use these commercial expression vectors and systems or others to produce WIP-1 routine techniques and readily available starting materials. (See e.g., Sambrook et al., *Molecular Cloning a Laboratory Manual*, Second Ed. Cold Spring Harbor Press (1989) which is incorporated herein by reference.) Thus, the desired proteins can be prepared in both prokaryotic and eukaryotic systems, resulting in a spectrum of processed forms of the protein.

One having ordinary skill in the art may use other commercially available expression vectors and systems or produce vectors using well known methods and readily available starting materials. Expression systems containing the requisite control sequences, such as promoters and polyadenylation signals, and preferably enhancers, are readily available and known in the art for a variety of hosts. See e.g., Sambrook et al., *Molecular Cloning a Laboratory Manual*, Second Ed. Cold Spring Harbor Press (1989).

The expression vector including the DNA that encodes WIP-1 is used to transform the compatible host which is then cultured and maintained under conditions wherein expression of the foreign DNA takes place. The protein of the present invention thus produced is recovered from the culture, either by lysing the cells or from the culture medium as appropriate and known to those in the art. One having ordinary skill in the art can, using well known techniques, isolate WIP-1 that is produced using such expression systems. The methods of purifying WIP-1 from natural sources using antibodies which specifically bind to WIP-1 as described above, may be equally applied to purifying WIP-1 produced by recombinant DNA methodology.

Examples of genetic constructs include the WIP-1 coding sequence operably linked to a promoter that is functional in the cell line into which the constructs are transfected. Examples of constitutive promoters include promoters from cytomegalovirus or SV40. Examples of inducible promoters include mouse mammary leukemia virus or metallothionein promoters. Those having ordinary skill in the art can readily produce genetic constructs useful for transfecting with cells with DNA that encodes WIP-1 from readily available starting materials. Such gene constructs are useful for the production of WIP-1.

In addition to producing WIP-1 by recombinant techniques, automated peptide synthesizers may also be employed to produce WIP-1. Such techniques are well known to those having ordinary skill in the art and are useful if derivatives which have substitutions not provided for in DNA-encoded protein production.

In addition to producing WIP-1, PAP-1, WNV Cp and PIM-1 may be similarly produced and isolated to be used as reagents. The following sequences identified by accession number and references are incorporated herein by reference.

| gene | Accession number | Comments |
| --- | --- | --- |
| PAP-1 | NM 018739 | Mouse |
| PAP-1 | D78255 | Mouse |
| PIM-1 | M24779 | Human |
| PIM-1 | NM 002648 | Human |
| PIM-1 | XM 004317 | Human |
| PAPA-1 (WIP-1) | AB054538 | Human |
| PAPA-1 (WIP-1) | NM 031288 | Human |
| West Nile Virus | AF202541 | strain HNY1999 |
| West Nile Virus | NC 001563 | complete genome |

Nucleic acid molecules that encode WIP-1 may be delivered using any one of a variety of delivery components, such as recombinant viral expression vectors or other suitable delivery means, so as to affect their introduction and expression in compatible host cells. In general, viral vectors may be DNA viruses such as recombinant adenoviruses and recombinant vaccinia viruses or RNA viruses such as recombinant retroviruses. Other recombinant vectors include recombinant prokaryotes which can infect cells and express recombinant genes. In addition to recombinant vectors, other delivery components are also contemplated such as encapsulation in liposomes, transferrin-mediated transfection and other receptor-mediated means. The invention is intended to include such other forms of expression vectors and other suitable delivery means which serve equivalent functions and which become known in the art subsequently hereto.

The present invention is also directed to methods of inhibiting the expression of WIP-1 with oligonucleotides complementary to WIP-1 nucleic acid molecules. Oligonucleotides may comprise nucleotide sequences sufficient in identity and number to effect specific hybridization with a particular nucleic acid molecule. Such oligonucleotides are commonly described as "complementary to mRNA." Oligonucleotides may also be directed to nucleotide sequences within the genome. Oligonucleotides are commonly used as research reagents and diagnostics. Oligonucleotides have been employed as therapeutic moieties in the treatment of disease states in animals and man.

According to the present invention, preferred intragenic site for antisense oligonucleotides is the region encompassing the translation initiation or termination codon of the open reading frame (ORF) of the gene. Other target regions include the 5' untranslated region (5'UTR) and the 3' untranslated region (3'UTR). mRNA splice sites may also be preferred target regions. Once the target site has been identified, oligonucleotides are chosen which are sufficiently complementary to the target, i.e., hybridize sufficiently well and with sufficient specificity, to give the desired effect.

According to the present invention, "oligonucleotide" refers to oligomer(s) or polymer(s) of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Modified or substituted oligonucleotides are often preferred because of desirable properties such as, for example, enhanced cellular uptake, enhanced affinity for nucleic acid target and increased stability in the presence of nucleases.

Preferred oligonucleotides include, for example, phosphorothioates, phosphotriesters, and methyl phosphonates. Oligonucleotides may also contain one or more substituted sugar moieties including, but not limited to, 2'-OH, halogen, and alkyl. Oligonucleotides of the invention may also include nucleobase modifications or substitutions. As used herein, "unmodified" or "natural" nucleobases include adenine (A), guanine (G), thymine (T), cytosine (C) and uracil (U). Modified nucleobases include, for example, hypoxanthine, 6-methyladenine, 5-me pyrimidines, 2-aminoadenine, and the like.

The oligonucleotides in accordance with this invention may comprise from about 8 to about 150 nucleotides. More preferably, the oligonucleotides preferably comprise from about 8 to about 100 nucleotides. More preferably, the oligonucleotides preferably comprise from about 8 to about 50 nucleotides. More preferably, the oligonucleotides preferably comprise from about 8 to about 30 nucleotides. It is more preferred that such oligonucleotides comprise from about 12 to 25 nucleotides.

The oligonucleotides of the present invention can be utilized as diagnostics, therapeutics and as research reagents and kits. For therapeutics, an animal, preferably a human, suspected of having a disease or disorder which can be treated by modulating the expression of WIP-1 is treated by administering oligonucleotides in accordance with this invention. The oligonucleotides of the invention can be utilized in pharmaceutical compositions by adding an effective amount of an oligonucleotide to a suitable pharmaceutically acceptable diluent or carrier. Use of the oligonucleotides and methods of the invention may also be useful prophylactically.

The oligonucleotides of the present invention can be used as diagnostics for the presence of WIP-1-specific nucleic acids in a cell or tissue sample. For example, radiolabeled oligonucleotides can be prepared by $^{32}$P labeling at the 5' end with polynucleotide kinase. Sambrook et al., *Molecular Cloning: A Laboratory Manual*, Cold Spring Harbor Laboratory, 1989, Volume 2, pg. 10.59. Radiolabeled oligonucleotides are then contacted with cell or tissue samples suspected of containing WIP-1 mRNA, and the samples are washed to remove unbound oligonucleotide. Radioactivity remaining in the sample indicates the presence of bound oligonucleotide, which in turn indicates the presence of nucleic acids complementary to the oligonucleotide, and can be quantitated using a scintillation counter or other routine means. Expression of nucleic acids encoding these proteins is thus detected.

Radiolabeled oligonucleotides of the present invention can also be used to perform autoradiography of issues to determine the localization, distribution and quantitation of WIP-1 for research, diagnostic or therapeutic purposes. In such studies, tissue sections are treated with radiolabeled oligonucleotide and washed as described above, then exposed to photographic emulsion according to routine autoradiography procedures. The emulsion, when developed, yields an image of silver grains over the regions expressing a WIP-1 gene. Quantitation of the silver grains permits detection of the expression of mRNA molecules encoding WIP-1 proteins and permits targeting of oligonucleotides to these areas.

Oligonucleotides, or vectors producing the same, can be formulated into pharmaceutical compositions. Pharmaceutical compositions according to the invention include delivery components in combination with nucleic acid molecules which further comprise a pharmaceutically acceptable carriers or vehicles, such as, for example, saline. Any medium may be used which allows for successful delivery of the nucleic acid. One skilled in the art would readily comprehend the multitude of pharmaceutically acceptable media that may be used in the present invention. Suitable pharmaceutical carriers are described in *Remington's Pharmaceutical Sciences*, A. Osol, a standard reference text in this field, which is incorporated herein by reference.

In some embodiments, pharmaceutical compositions comprise Wip-1 or fragments thereof. In preferred embodiments the fragments bind to WNV Cp. In preferred embodiments the fragments are soluble, that is they may be injected into body fluid, particularly blood as a soluble component. Fragments comprise at least 8, preferably more than 10 amino acids from Wip-1 and may comprise non-Wip-1 sequences. In some embodiments, fragments comprise at least 15, preferably more than 20, more preferably 25 or more, more preferably 30 or more, more preferably 40 or more, more preferably 50, more preferably 60 or more, more preferably 70 or more, more preferably 80 or more, more preferably 90 or more, more preferably 100 or more, more preferably 105 or more, more preferably 110 or more, more preferably 120 or more or more, more preferably 130 or more, more preferably 140 or more, more than 150 or more, more preferably 160 or more, more preferably 170 or more, more preferably 180 or more, more preferably 190 or more, more preferably 200 or more, more preferably 210, more preferably 220 or more, more preferably 230 or more, more preferably 240 or more, more preferably 250 or more, more preferably 260 or more, more preferably 270 or more, more preferably 280 or more, more preferably 290 or more, more preferably 300 or more, more preferably 320 or more, more preferably 330. Fragments may comprise amino acids from Wip-1 and may comprise non-Wip-1 sequences. Pharmaceutical compositions are preferably injectable compositions which are sterile and pyrogen free.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Compositions for oral administration include powders or granules, suspensions or solutions in water or non-aqueous media, capsules, sachets or tablets. Thickeners, flavoring agents, diluents, emulsifiers, dispersing aids or binders may be desirable. Compositions for parenteral, intravenous, intrathecal or intraventricular administration may include sterile aqueous solutions which may also contain buffers, diluents and other suitable additives and are preferably sterile and pyrogen free. Pharmaceutical compositions which are suitable for intravenous administration according to the invention are sterile and pyrogen free.

The pharmaceutical compositions of the present invention may be administered by any means that enables the active agent to reach the agent's site of action in the body of a mammal. The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip, subcutaneous, intraperitoneal or intramuscular injection, pulmonary administration, e.g., by inhalation or insufflation, or intrathecal or intraventricular administration.

Dosage varies depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Formulation of therapeutic compositions and their subsequent administration is believed to be within the skill of those in the art.

Hybridomas which produce antibodies that bind to WIP-1, and the antibodies themselves, are useful in the isolation and purification of WIP-1 and protein complexes that include WIP-1. In addition, antibodies are specific inhibitors of WIP-1 activity. Antibodies which specifically bind to WIP-1 may be used to purify the protein from natural sources using well known techniques and readily available starting materials. Such antibodies may also be used to purify the protein from material present when producing the protein by recombinant DNA methodology.

As used herein, the term "antibody" is meant to refer to complete, intact antibodies, and Fab fragments and F(ab)$_2$ fragments thereof. Complete, intact antibodies include monoclonal antibodies such as murine monoclonal antibodies, chimeric antibodies and humanized antibodies. In some embodiments, the antibodies specifically bind to an epitope of WIP-1. Antibodies that bind to an epitope is useful to isolate and purify that protein from both natural sources or recombinant expression systems using well known techniques such as affinity chromatography. Such antibodies are useful to detect the presence of such protein in a sample and to determine if cells are expressing the protein.

The production of antibodies and the protein structures of complete, intact antibodies, Fab fragments and F(ab)$_2$ fragments and the organization of the genetic sequences that encode such molecules are well known and are described, for example, in Harlow, E. and D. Lane (1988) *ANTIBODIES. A Laboratory Manual*, Cold Spring Harbor Laboratory, Cold Spring Harbor, N.Y. which is incorporated herein by reference. Briefly, for example, WIP-1, or an immunogenic fragment thereof, is injected into mice. The spleen of the mouse is removed, the spleen cells are isolated and fused with immortalized mouse cells. The hybrid cells, or hybridomas, are cultured and those cells which secrete antibodies are selected. The antibodies are analyzed and, if found to specifically bind to WIP-1, the hybridoma which produces them is cultured to produce a continuous supply of antibodies.

Another aspect of the present invention relates to methods of identifying anti-WNV compounds. According to this aspect, the WIP-1 or a fragment of WIP-1 known to interact with Cp is contacted with Cp or a fragment of Cp which interacts with WIP-1 to prevent or inhibit G2/M transition by cells in the presence of a test compound. The affinity of the WIP-1 or a fragment of WIP-1 known to interact with Cp to the Cp or fragment thereof is measured and compared to the affinity of the WIP-1 or a fragment of WIP-1 known to interact with Cp to the Cp or fragment thereof in the absence of a test compound. Compounds which can disrupt the binding of Cp to PAP1 may be useful as anti-WNV compounds. An example of a positive control in this drug screen assay would be anti-WIP-1 antibodies which competitively bind to WIP-1 with respect to Cp. Another example of a positive control in this drug screen assay would be anti-Cp antibodies which competitively bind to Cp with respect to WIP-1. Such antibodies are useful as known compounds that disrupt the Cp/WIP-1 interaction. Known quantities of Cp and WIP-1 may be combined under conditions suitable for binding. In some embodiments of the invention, the preferred concentration of test compound is between 1 µM and 500 µM. A preferred concentration is 10 µM to 100 µM. In some preferred embodiments, it is desirable to use a series of dilutions of test compounds.

Another aspect of the present invention relates to methods of identifying compounds that inhibit WIP-1/PAP-1 interaction and therefore induce apoptosis in cells which have such molecular complexes. According to this aspect, the WIP-1 or a fragment of WIP-1 known to interact with PAP-1 is contacted with PAP-1 or a fragment of PAP-1 which interacts with WIP-1. The affinity of the WIP-1 or a fragment thereof to PAP-1 or fragment thereof is measured and compared to the affinity of the WIP-1 or a fragment thereof to the PAP-1 or fragment thereof in the absence of a test compound. Compounds which can disrupt the binding of PAP-1 to WIP-1 may be useful as anti-cancer compounds. An example of a positive control in this drug screen assay would be anti-WIP-1 antibodies which competitively bind to WIP-1 with respect to PAP-1. Another example of a positive control in this drug screen assay would be anti-PAP-1 antibodies which competitively bind to PAP-1 with respect to WIP-1. Such antibodies are useful as known compounds that disrupt the PAP-1/WIP-1 interaction. Known quantities of PAP-1 and WIP-1 may be combined under conditions suitable for binding. In some embodiments of the invention, the preferred concentration of test compound is between 1 µM and 500 µM. A preferred concentration is 10 µM to 100 µM. In some preferred embodiments, it is desirable to use a series of dilutions of test compounds.

The present invention is further illustrated by the following examples, which are not intended to be limiting in any way.

EXAMPLE

West Nile Virus is a single-stranded RNA virus with a positive-polarity RNA genome of approximately 11 kb. The nucleocapsid of approximately 30 nm in diameter consists of capsid and genomic RNA. The cloning and expression of cDNA encoding WNV Capsid (Cp), and the use of WNVCP-DNA as an immunogen in mice has been reported. Characterization of the WNV Cp revealed that it is a pathogenic protein, which induce apoptosis, in vitro and in vivo through the mitochondrial-mediated pathway. In a search for the cellular proteins that may act as possible intracellular receptor for this capsid protein using a yeast-two hybrid system, a human cDNA encoding a novel 343 aa protein, interacted by Cp and we have tentatively designated as WIP-1 (West Nile capsid interacting protein) was identified. For immunoblotting purposes, an HA epitope was fused in frame to the amino terminal end of this protein. In vitro translated protein product prepared from pcWip revealed the synthesis of protein of about 38-kDa in mass. The physical interaction between WNV Cp and its ligand was confirmed by using $^{35}$S-labeled in vitro translated protein. The SDS gel analysis of lysate prepared from the cells transfected with this expression plasmid followed by brief metabolic labeling of cells using $^{35}$S-labeled methionine indicated the mobility of protein corresponding to molecular mass of in vitro translated product. Transient expression studies indicate that this protein is clearly localized in the cytoplasmic region with a typical donut structure localized at the perinuclear region. In most of the cells expressing both Cp and its ligand, WIP is colocalized with the Cp protein in the nuclear region. This indicates a clear interaction between these proteins inside the cells. Several deletion as well as site-specific mutants of both Cp and its ligand have been constructed in order map their interaction domains. Some of these site-directed mutants have exhibited totally altered localization patterns.

The invention claimed is:

1. A recombinant expression vector comprising a nucleic acid sequence that encodes a protein having the amino acid sequence of human West Nile Virus Core Protein/Capsid Interacting Protein human WIP-1.

2. A host cell comprising the recombinant expression vector of claim 1.

3. An isolated nucleic acid molecule consisting of the human West Nile Virus Core Protein/Capsid Interacting Protein human WIP-1 cDNA sequence or a fragment thereof that encodes a fragment of human West Nile Virus Core Protein/Capsid Interacting Protein human WIP-1 having at least 120 amino acids.

4. An isolated oligonucleotide molecule of no more than 150 nucleotides comprising a nucleotide sequence complementary to the human West Nile Virus Core Protein/Capsid Interacting Protein human (WIP-1) cDNA sequence, wherein the nucleotide sequence complementary to human WIP-1 cDNA sequence is complementary to no more than between 24 to 100 nucleotides of the human WIP-1 cDNA sequence.

5. An isolated oligonucleotide molecule of no more than 150 nucleotides comprising of a nucleotide sequence complementary to a nucleotide sequence of about 150 nucleotides of the human West Nile Virus Core Protein/Capsid Interacting Protein human WIP-1 cDNA sequence.

6. An isolated oligonucleotide molecule consisting of a nucleotide sequence complementary to a nucleotide sequence of 28 nucleotides of the human West Nile Virus Core Protein/Capsid Interacting Protein human WIP-1 cDNA sequence.

7. A recombinant expression vector comprising a nucleic acid sequence that encodes SEQ ID NO:3.

8. An isolated nucleic acid molecule consisting of the West Nile Virus Core Protein/Capsid Interacting Protein WIP-1 cDNA sequence or a fragment thereof that encodes a fragment of SEQ ID NO:3 having at least 120 amino acids.

9. The oligonucleotide molecule of claim 4 wherein said human West Nile Virus Core Protein/Capsid Interacting Protein human WIP-1 cDNA sequence is SEQ ID NO:3.

10. The isolated nucleic acid molecule of claim 3 consisting of the cDNA sequence of human West Nile Virus Core Protein/Capsid Interacting Protein human WIP-1.

11. The isolated oligonucleotide molecule of claim 4 consisting of a nucleotide sequence complementary to no more than between 24 to 50 nucleotides of the human West Nile Virus Core Protein/Capsid Interacting Protein human WIP-1 cDNA sequence.

* * * * *

UNITED STATES PATENT AND TRADEMARK OFFICE
CERTIFICATE OF CORRECTION

| | | |
|---|---|---|
| PATENT NO. | : 7,625,751 B2 | Page 1 of 1 |
| APPLICATION NO. | : 10/478743 | |
| DATED | : December 1, 2009 | |
| INVENTOR(S) | : Weiner et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1039 days.

Signed and Sealed this

Second Day of November, 2010

David J. Kappos
*Director of the United States Patent and Trademark Office*

SEQUENCE LISTING

<160> NUMBER OF SEQ ID NOS: 4

<210> SEQ ID NO 1
<211> LENGTH: 1160
<212> TYPE: DNA
<213> ORGANISM: Artificial Sequence
<220> FEATURE:
<223> OTHER INFORMATION: Synthetic Construct

<400> SEQUENCE: 1

```
accatgccat acgacgtacc agattacgct catatggagg cccctgagcc gggagaagcc    60
ctggagttga gcctggcggg tgcccatggc catggagtgc acaagaaaaa acacaagaag   120
cacaagaaga aacacaagaa gaaacaccat caggaagaag acgccgggcc cacgcagccg   180
tcccctgcca agcctcagct caaactcaaa atcaagcttg ggggacaagt cctggggacc   240
aagagtgttc ctaccttcac tgtgatccca gaggggcctc gctcaccctc tcccttatg    300
gttgtgata atgaagagga acctatgaa ggagtccccc ttgagcagta ccgtgcctgg    360
ctggatgaag acagtaatct ctctccctct ccacttcggg acctatcagg agggttaggg   420
ggtcaggagg aagaggagga acagaggtgg ctggatgccc tggagaaggg ggagctggat   480
gacaatggag acctcaagaa ggagatcaat gagcggctgc ttactgctcg acagcgagct   540
ctgctccaga aggcgcggag tcaaccttcc cctatgctgc cgctgcctgt agctgagggc   600
tgcccacctc ccgccctcac agaggagatg ctgctgaagc gcgaggagcg ggcgcggaag   660
cggcggctcc aggcggcgcg gcgggcagaa gagcacaaga accagactat cgagcgcctc   720
accaagactg cggcgaccag tgggcgggga ggccgggggg gcgcacgggg cgagcggcgg   780
ggagggcggg ctgcggctcc ggcccccatg gtgcgctact gcagcggagc acagggttcc   840
accctttcct tcccacctgg cgtccccgcc cccacggcag tgtctcagcg gccatccccc   900
tcaggcccgc cgccgcgctg ctctgtcccc ggctgtcccc atccgcgccg ctacgcttgc   960
tcccgcacag gccaggcact ctgtagtctt cagtgctacc gcatcaacct gcagatgcgg  1020
ctgggggggc ccgagggtcc tggatccccc cttttggcta cgtaaggccc ttaacccgga  1080
ctctgcgccc cgtcccatgc ccgctcttga gtatcttccc caccctatta aattacatcc  1140
ggtgcaaaaa aaaaaaaaaa                                              1160
```

<210> SEQ ID NO 2
<211> LENGTH: 382
<212> TYPE: PRT
<213> ORGANISM: Artificial Sequence
<220> FEATURE:
<223> OTHER INFORMATION: Synthetic Construct

<400> SEQUENCE: 2

Thr Met Pro Tyr Asp Val Pro Asp Tyr Ala His Met Glu Ala Pro Glu
1               5                   10                  15

Pro Gly Glu Ala Leu Glu Leu Ser Leu Ala Gly Ala His Gly His Gly
            20                  25                  30

Val His Lys Lys Lys His Lys Lys His Lys Lys His Lys Lys Lys
        35                  40                  45

His His Gln Glu Glu Asp Ala Gly Pro Thr Gln Pro Ser Pro Ala Lys
    50                  55                  60

Pro Gln Leu Lys Leu Lys Ile Lys Leu Gly Gly Gln Val Leu Gly Thr

```
                 65                  70                  75                  80
Lys Ser Val Pro Thr Phe Thr Val Ile Pro Glu Gly Pro Arg Ser Pro
                     85                  90                  95
Ser Pro Leu Met Val Val Asp Asn Glu Glu Pro Met Glu Gly Val
                100                 105                 110
Pro Leu Glu Gln Tyr Arg Ala Trp Leu Asp Glu Asp Ser Asn Leu Ser
                115                 120                 125
Pro Ser Pro Leu Arg Asp Leu Ser Gly Gly Leu Gly Gln Glu Glu
            130                 135                 140
Glu Glu Glu Gln Arg Trp Leu Asp Ala Leu Glu Lys Gly Glu Leu Asp
145                 150                 155                 160
Asp Asn Gly Asp Leu Lys Lys Glu Ile Asn Glu Arg Leu Leu Thr Ala
                165                 170                 175
Arg Gln Arg Ala Leu Leu Gln Lys Ala Arg Ser Gln Pro Ser Pro Met
                180                 185                 190
Leu Pro Leu Pro Val Ala Glu Gly Cys Pro Pro Ala Leu Thr Glu
            195                 200                 205
Glu Met Leu Leu Lys Arg Glu Glu Arg Ala Arg Lys Arg Arg Leu Gln
210                 215                 220
Ala Ala Arg Arg Ala Glu Glu His Lys Asn Gln Thr Ile Glu Arg Leu
225                 230                 235                 240
Thr Lys Thr Ala Ala Thr Ser Gly Arg Gly Arg Gly Arg Gly Ala Arg
                245                 250                 255
Gly Glu Arg Arg Gly Gly Arg Ala Ala Ala Pro Ala Pro Met Val Arg
                260                 265                 270
Tyr Cys Ser Gly Ala Gln Gly Ser Thr Leu Ser Phe Pro Pro Gly Val
                275                 280                 285
Pro Ala Pro Thr Ala Val Ser Gln Arg Pro Ser Pro Ser Gly Pro Pro
            290                 295                 300
Pro Arg Cys Ser Val Pro Gly Cys Pro His Pro Arg Arg Tyr Ala Cys
305                 310                 315                 320
Ser Arg Thr Gly Gln Ala Leu Cys Ser Leu Gln Cys Tyr Arg Ile Asn
                325                 330                 335
Leu Gln Met Arg Leu Gly Gly Pro Glu Gly Pro Gly Ser Pro Leu Leu
                340                 345                 350
Ala Thr Gly Pro Pro Gly Leu Cys Ala Pro Ser His Ala Arg Ser Val
                355                 360                 365
Ser Ser Pro Pro Tyr Ile Thr Ser Gly Ala Lys Lys Lys Lys
            370                 375                 380

<210> SEQ ID NO 3
<211> LENGTH: 1164
<212> TYPE: DNA
<213> ORGANISM: Homo sapiens
<220> FEATURE:
<221> NAME/KEY: CDS
<222> LOCATION: (38)..(1069)

<400> SEQUENCE: 3
gggtaagctg tggcggcgtg ggagcacctc tggggct atg gag gcc cct gag ccg       55
                                        Met Glu Ala Pro Glu Pro
                                         1               5 gga gaa gcc ctg gag ttg agc ctg gcg ggt gcc cat ggc cat gga gtg      103
Gly Glu Ala Leu Glu Leu Ser Leu Ala Gly Ala His Gly His Gly Val
                 10                  15                  20 cac aag aaa aaa cac aag aag cac aag aag aaa cac aag aag aaa cac      151
```

```
              His Lys Lys Lys His Lys Lys His Lys Lys Lys His Lys Lys His
                      25                  30                  35 cat cag gaa gaa gac gcc ggg ccc acg cag ccg tcc cct gcc aag cct         199
His Gln Glu Glu Asp Ala Gly Pro Thr Gln Pro Ser Pro Ala Lys Pro
         40                  45                  50 cag ctc aaa ctc aaa atc aag ctt ggg gga caa gtc ctg ggg acc aag         247
Gln Leu Lys Leu Lys Ile Lys Leu Gly Gly Gln Val Leu Gly Thr Lys
 55                  60                  65                  70 agt gtt cct acc ttc act gtg atc cca gag ggg cct cgc tca ccc tct         295
Ser Val Pro Thr Phe Thr Val Ile Pro Glu Gly Pro Arg Ser Pro Ser
                 75                  80                  85 ccc ctt atg gtt gtg gat aat gaa gag gaa cct atg gaa gga gtc ccc         343
Pro Leu Met Val Val Asp Asn Glu Glu Glu Pro Met Glu Gly Val Pro
             90                  95                 100 ctt gag cag tac cgt gcc tgg ctg gat gaa gac agt aat ctc tct ccc         391
Leu Glu Gln Tyr Arg Ala Trp Leu Asp Glu Asp Ser Asn Leu Ser Pro
            105                 110                 115 tct cca ctt cgg gac cta tca gga ggg tta ggg ggt cag gag gaa gag         439
Ser Pro Leu Arg Asp Leu Ser Gly Gly Leu Gly Gly Gln Glu Glu Glu
        120                 125                 130 gag gaa cag agg tgg ctg gat gcc ctg gag aag ggg gag ctg gat gac         487
Glu Glu Gln Arg Trp Leu Asp Ala Leu Glu Lys Gly Glu Leu Asp Asp
135                 140                 145                 150 aat gga gac ctc aag aag gag atc aat gag cgg atg ctt act gct cga         535
Asn Gly Asp Leu Lys Lys Glu Ile Asn Glu Arg Met Leu Thr Ala Arg
                155                 160                 165 cag cga gct ctg ctc cag aag gcg cgg agt caa cct tcc cct atg ctg         583
Gln Arg Ala Leu Leu Gln Lys Ala Arg Ser Gln Pro Ser Pro Met Leu
            170                 175                 180 ccg ctg cct gta gct gag ggc tgc cca cct ccc gcc ctc aca gag gag         631
Pro Leu Pro Val Ala Glu Gly Cys Pro Pro Pro Ala Leu Thr Glu Glu
        185                 190                 195 atg ctg ctg aag cgc gag gag cgg gcg cgg aag cgg cgg ctc cag gcg         679
Met Leu Leu Lys Arg Glu Glu Arg Ala Arg Lys Arg Arg Leu Gln Ala
    200                 205                 210 gcg cgg cgg gca gaa gag cac aag aac cag act atc gag cgc ctc acc         727
Ala Arg Arg Ala Glu Glu His Lys Asn Gln Thr Ile Glu Arg Leu Thr
215                 220                 225                 230 aag act gcg gcg acc agt ggg cgg gga ggc cgg ggg ggc gca cgg ggc         775
Lys Thr Ala Ala Thr Ser Gly Arg Gly Gly Arg Gly Gly Ala Arg Gly
                235                 240                 245 gag cgg cgg gga ggg cgg gct gcg gct ccg gcc ccc atg gtg cgc tac         823
Glu Arg Arg Gly Gly Arg Ala Ala Ala Pro Ala Pro Met Val Arg Tyr
            250                 255                 260 tgc agc gga gca cag ggt tcc acc ctt tcc ttc cca cct ggc gtc ccc         871
Cys Ser Gly Ala Gln Gly Ser Thr Leu Ser Phe Pro Pro Gly Val Pro
        265                 270                 275 gcc ccc acg gca gtg tct cag cgg cca tcc ccc tca ggc ccg ccg ccg         919
Ala Pro Thr Ala Val Ser Gln Arg Pro Ser Pro Ser Gly Pro Pro Pro
    280                 285                 290 cgc tgc tct gtc ccc ggc tgt ccc cat ccg cgc cgc tac gct tgc tcc         967
Arg Cys Ser Val Pro Gly Cys Pro His Pro Arg Arg Tyr Ala Cys Ser
295                 300                 305                 310 cgc aca ggc cag gca ctc tgt agt ctt cag tgc tac cgc atc aac ctg        1015
Arg Thr Gly Gln Ala Leu Cys Ser Leu Gln Cys Tyr Arg Ile Asn Leu
                315                 320                 325 cag ctg cgg ctg ggg ggg ccc gag ggt cct gga tcc ccc ctt ttg gct        1063
Gln Leu Arg Leu Gly Gly Pro Glu Gly Pro Gly Ser Pro Leu Leu Ala
            330                 335                 340
```

```
acg taa ggcccttaac ccggactctg cgccccgtcc catgcccgct cttgagtatc    1119
Thr ttccccaccc tattaaatta catccggtgc aaaaaaaaaa aaaaa              1164
```

<210> SEQ ID NO 4
<211> LENGTH: 343
<212> TYPE: PRT
<213> ORGANISM: Homo sapiens

<400> SEQUENCE: 4

```
Met Glu Ala Pro Glu Pro Gly Glu Ala Leu Glu Leu Ser Leu Ala Gly
  1               5                  10                  15

Ala His Gly His Gly Val His Lys Lys His Lys Lys His Lys Lys
             20                  25                  30

Lys His Lys Lys His His Gln Glu Asp Ala Gly Pro Thr Gln
         35                  40                  45

Pro Ser Pro Ala Lys Pro Gln Leu Lys Leu Lys Ile Lys Leu Gly Gly
 50                  55                  60

Gln Val Leu Gly Thr Lys Ser Val Pro Thr Phe Thr Val Ile Pro Glu
 65                  70                  75                  80

Gly Pro Arg Ser Pro Ser Pro Leu Met Val Val Asp Asn Glu Glu Glu
             85                  90                  95

Pro Met Glu Gly Val Pro Leu Glu Gln Tyr Arg Ala Trp Leu Asp Glu
            100                 105                 110

Asp Ser Asn Leu Ser Pro Ser Pro Leu Arg Asp Leu Ser Gly Gly Leu
            115                 120                 125

Gly Gly Gln Glu Glu Glu Glu Gln Arg Trp Leu Asp Ala Leu Glu
        130                 135                 140

Lys Gly Glu Leu Asp Asp Asn Gly Asp Leu Lys Lys Glu Ile Asn Glu
145                 150                 155                 160

Arg Met Leu Thr Ala Arg Gln Arg Ala Leu Leu Gln Lys Ala Arg Ser
                165                 170                 175

Gln Pro Ser Pro Met Leu Pro Leu Pro Val Ala Glu Gly Cys Pro Pro
            180                 185                 190

Pro Ala Leu Thr Glu Glu Met Leu Leu Lys Arg Glu Glu Arg Ala Arg
            195                 200                 205

Lys Arg Arg Leu Gln Ala Ala Arg Arg Ala Glu His Lys Asn Gln
        210                 215                 220

Thr Ile Glu Arg Leu Thr Lys Thr Ala Ala Thr Ser Gly Arg Gly
225                 230                 235                 240

Arg Gly Gly Ala Arg Gly Glu Arg Arg Gly Gly Arg Ala Ala Pro
                245                 250                 255

Ala Pro Met Val Arg Tyr Cys Ser Gly Ala Gln Gly Ser Thr Leu Ser
            260                 265                 270

Phe Pro Pro Gly Val Pro Ala Pro Thr Ala Val Ser Gln Arg Pro Ser
            275                 280                 285

Pro Ser Gly Pro Pro Arg Cys Ser Val Pro Gly Cys Pro His Pro
        290                 295                 300

Arg Arg Tyr Ala Cys Ser Arg Thr Gly Gln Ala Leu Cys Ser Leu Gln
305                 310                 315                 320

Cys Tyr Arg Ile Asn Leu Gln Leu Arg Leu Gly Gly Pro Glu Gly Pro
                325                 330                 335

Gly Ser Pro Leu Leu Ala Thr
            340
```